US008753275B2

(12) United States Patent
Najafi et al.

(10) Patent No.: US 8,753,275 B2
(45) Date of Patent: Jun. 17, 2014

(54) INTELLIGENT DEVICE TO MONITOR AND REMIND PATIENTS WITH FOOTWEAR, WALKING AIDS, BRACES, OR ORTHOTICS

(75) Inventors: Bijan Najafi, Highland Park, IL (US); Ali-Reza Boloori, Los Angeles, CA (US); James Wrobel, Grayslake, IL (US)

(73) Assignees: BioSensics LLC, Cambridge, MA (US); Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 13/005,548

(22) Filed: Jan. 13, 2011

(65) Prior Publication Data
US 2012/0184878 A1 Jul. 19, 2012

(51) Int. Cl.
G08B 1/08 (2006.01)
A61B 5/00 (2006.01)

(52) U.S. Cl.
USPC ............. 600/301; 340/539.1; 340/539.11; 340/539.12; 36/114; 482/4; 482/8; 600/587; 600/592; 602/19; 602/23

(58) Field of Classification Search
USPC ............ 340/539.1, 539.11, 539.12; 36/114; 600/301, 592, 587; 602/19, 23; 482/4, 482/8
See application file for complete search history.

(56) References Cited

U.S. PATENT DOCUMENTS

| | | | | |
|---|---|---|---|---|
| 3,702,999 A | * | 11/1972 | Gradisar | 340/573.1 |
| 5,373,651 A | * | 12/1994 | Wood | 36/114 |
| 5,396,227 A | * | 3/1995 | Carroll et al. | 340/573.4 |
| 5,642,096 A | * | 6/1997 | Leyerer et al. | 340/573.1 |
| 5,907,819 A | | 5/1999 | Johnson | |
| 6,119,516 A | | 9/2000 | Hock | |
| 6,201,476 B1 | | 3/2001 | Depeursinge et al. | |
| 6,433,690 B2 | | 8/2002 | Petelenz et al. | |
| 6,730,024 B2 | * | 5/2004 | Freyre et al. | 600/300 |
| 6,890,285 B2 | * | 5/2005 | Rahman et al. | 482/8 |
| 6,926,667 B2 | * | 8/2005 | Khouri | 600/300 |
| 6,997,882 B1 | | 2/2006 | Parker et al. | |
| 7,141,026 B2 | | 11/2006 | Aminian et al. | |
| 7,166,063 B2 | * | 1/2007 | Rahman et al. | 482/8 |
| 7,334,472 B2 | | 2/2008 | Seo et al. | |
| 7,620,450 B2 | | 11/2009 | Kim et al. | |
| 7,627,450 B2 | | 12/2009 | Lee et al. | |

(Continued)

FOREIGN PATENT DOCUMENTS

EP 1195139 A1 4/2002
WO WO 03/065891 A2 8/2003

OTHER PUBLICATIONS

American Diabetes Association, Apr. 7-8, 1999, Boston, Massachusetts, "Consensus development conference in diabetic foot wound care", Diabetes Care 22.8:1354 (Aug. 1999).

(Continued)

Primary Examiner — Sean Dougherty
(74) Attorney, Agent, or Firm — Knobbe, Martens, Olson & Bear, LLP

(57) ABSTRACT

A system is provided for monitoring whether a user is wearing and/or using a tagged device such as prescribed footwear, a walking aid, a brace or other orthotics. The system may detect whether the user is using a tagged device and can, in some embodiments, alert the user or the user's caregivers if the user ambulates without using the tagged device.

21 Claims, 3 Drawing Sheets

(56) References Cited

U.S. PATENT DOCUMENTS

| | | | |
|---|---|---|---|
| 7,632,216 B2* | 12/2009 | Rahman et al. | 482/8 |
| 7,634,379 B2 | 12/2009 | Noble | |
| 7,640,134 B2 | 12/2009 | Park et al. | |
| 7,701,354 B2* | 4/2010 | Chung | 340/573.7 |
| 7,725,289 B2 | 5/2010 | Nagashima et al. | |
| 7,747,409 B2 | 6/2010 | Ladetto et al. | |
| 7,771,371 B2* | 8/2010 | Avni | 600/592 |
| 7,857,771 B2 | 12/2010 | Alwan et al. | |
| 7,962,308 B2 | 6/2011 | Makino | |
| 7,983,872 B2 | 7/2011 | Makino et al. | |
| 8,007,450 B2 | 8/2011 | Williams | |
| 8,025,632 B2* | 9/2011 | Einarsson | 602/23 |
| 8,206,325 B1 | 6/2012 | Najafi et al. | |
| 8,242,879 B2* | 8/2012 | Haynes et al. | 340/4.1 |
| 8,384,551 B2* | 2/2013 | Ross et al. | 340/573.7 |
| 8,388,553 B2* | 3/2013 | James et al. | 600/587 |
| 2003/0065409 A1 | 4/2003 | Raeth et al. | |
| 2003/0078528 A1* | 4/2003 | Rahman et al. | 602/5 |
| 2003/0139692 A1 | 7/2003 | Barrey et al. | |
| 2004/0015103 A1 | 1/2004 | Aminian et al. | |
| 2005/0043660 A1* | 2/2005 | Stark et al. | 602/19 |
| 2005/0165336 A1* | 7/2005 | Rahman et al. | 602/1 |
| 2006/0140425 A1* | 6/2006 | Berg et al. | 381/312 |
| 2006/0166157 A1* | 7/2006 | Rahman et al. | 433/6 |
| 2006/0270949 A1 | 11/2006 | Mathie et al. | |
| 2007/0149359 A1* | 6/2007 | Rahman et al. | 482/4 |
| 2007/0270214 A1 | 11/2007 | Bentley | |
| 2007/0293781 A1* | 12/2007 | Sims et al. | 600/534 |
| 2008/0091762 A1* | 4/2008 | Neuhauser et al. | 709/201 |
| 2008/0281555 A1 | 11/2008 | Godin et al. | |
| 2008/0281636 A1* | 11/2008 | Jung et al. | 705/3 |
| 2008/0318683 A1* | 12/2008 | Rofougaran et al. | 463/39 |
| 2009/0002152 A1* | 1/2009 | Chung | 340/539.11 |
| 2009/0024065 A1* | 1/2009 | Einarsson | 602/26 |
| 2009/0055223 A1* | 2/2009 | Jung et al. | 705/3 |
| 2009/0058660 A1* | 3/2009 | Torch | 340/573.1 |
| 2009/0069724 A1 | 3/2009 | Otto et al. | |
| 2009/0076345 A1* | 3/2009 | Manicka et al. | 600/301 |
| 2009/0099495 A1* | 4/2009 | Campos et al. | 602/27 |
| 2009/0192414 A1 | 7/2009 | Yasuhara | |
| 2009/0195350 A1* | 8/2009 | Tsern et al. | 340/3.1 |
| 2009/0234249 A1* | 9/2009 | Randolph | 600/592 |
| 2009/0292194 A1* | 11/2009 | Libbus et al. | 600/391 |
| 2009/0293319 A1* | 12/2009 | Avni | 36/132 |
| 2010/0121227 A1 | 5/2010 | Stirling et al. | |
| 2010/0286571 A1 | 11/2010 | Allum et al. | |
| 2010/0324455 A1* | 12/2010 | Rangel et al. | 600/592 |
| 2011/0054359 A1* | 3/2011 | Sazonov et al. | 600/595 |
| 2011/0115629 A1* | 5/2011 | Holler et al. | 340/572.1 |
| 2012/0022667 A1* | 1/2012 | Accinni et al. | 623/34 |
| 2013/0245785 A1* | 9/2013 | Accini et al. | 623/34 |

OTHER PUBLICATIONS

Unpublished U.S. Appl. No. 13/053,147, filed Mar. 21, 2011 including its prosecution history, the cited references, the Office Actions therein, Najafi et al.

Unpublished U.S. Appl. No. 13/531,313, filed Jun. 22, 2012, including its prosecution history, the cited references, the Office Actions therein, Najafi et al.

Unpublished U.S. Appl. No. 13/723,040, filed Dec. 20, 2012 including its prosecution history, the cited references, the Office Actions therein, Najafi et al.

Aminian et al., "Spatio-temporal parameters of gait measured by an ambulatory system using miniature gyroscopes," *Journal of Biomechanics*, vol. 35:689-699 (2002).

Aminian et al., "Temporal feature estimation during walking using miniature accelerometers: an analysis of gait improvement after hip arthroplasty," *Medical & Biological Engineering & Computing*, vol. 37:686-691 (1999).

Armstrong et al., "Activity patterns of patients with diabetic foot ulceration", Diabetes Care, vol. 26(9):2595-2597 (2003).

Armstrong et al., "Continuous activity monitoring in persons a high risk for diabetes-related lower-extremity amputation", Journal of the American Podiatric Medical Association, vol. 91:451-455 (2001).

Armstrong et al., "Evaluation of removable and irremovable cast walkers in the healing of diabetic foot wounds: a randomized controlled trial", Diabetes Care, vol. 28:551-4 (2005).

Armstrong et al., "Variability in activity may precede diabetic foot ulceration", Diabetes Care, vol. 27(8):1980-1984 (2004).

Bohannon et al., "Walking speed: reference values and correlates for older adults," *J Orthop Sports Phys Ther*, vol. 24:86-90 (1996).

Brand, Paul W., "The diabetic foot", Diabetes Mellitus, Theory and Practice, $3^{rd}$ Ed., Ellenberg M. Rifkin H., Ed. New York: Medical Examination Publishing, 1983, pp. 803-828.

Coleman et al., "The total contact cast, a therapy for plantar ulceration on insensitive feet", J.Am. Podiatr. Med. Assoc., vol. 74:548-552 (1984).

Cummings et al., "Forgetting falls. The limited accuracy of recall of falls in the elderly," *J Am Geriatr Soc*, vol. 36:613-6 (1988).

Doughty et al., "The design of a practical and reliable fall detector for community and institutional telecare," *J Telemed Telecare*, vol. 6 Suppl 1:S150-4 (2000).

Helm et al., "Total contact casting in diabetic patients with neuropathic foot ulcerations", Arch. Phys. Med. Rehabil., vol. 65:691-693 (1984).

Lavery et al., "Reducing dynamic foot pressures in high-risk diabetic subjects with foot ulcerations", Diabetes Care, vol. 19(8):818-821 (1996).

Lindemann et al., "Evaluation of a fall detector based on accelerometers: a pilot study," *Med Biol Eng Comput*, vol. 43:548-51 (2005).

Mizell, "Using gravity to estimate accelerometer orientation", Proceedings of the Seventh IEEE International Symposium on Wearable Computers, Computer Society (2003).

Najafi et al., "Ambulatory system for human motion analysis using a kinematic sensor: Monitoring of daily physical activity in the elderly," *Ieee Transactions on Biomedical Engineering*, vol. 50:711-723 (2003).

Najafi et al., "Measurement of standsit and sit-stand transitions using a miniature gyroscope and its application in fall risk evaluation in the elderly," *Ieee Transactions on Biomedical Engineering*, vol. 49:843-851 (2002).

Najafi et al., "A novel ambulatory device for continuous 24-H monitoring of physical activity in daily life", North American Congress on Biomechanics (NACOB), Michigan, 2008.

Noury et al., "A smart sensor based on rules and its evaluation in daily routines," presented at 25th Annual International Conference of the IEEE Eng. Med. Biol. Society (2003).

Oliver et al., "Development and evaluation of evidence based risk assessment tool (STRATIFY) to predict which elderly inpatients will fall: case-control and cohort studies," *Bmj*, vol. 315:1049-53 (1997).

Pecoraro et al., "Pathways to diabetic limb amputation", Diabetes Care, vol. 13(5):513-521 (1990).

Sinacore et al., "Diabetic plantar ulcers treated by total contact casting", Phys. Ther. vol. 67:1543-1547 (1987).

Tinetti et al., "Fall risk index for elderly patients based on number of chronic disabilities," *Am J Med*, vol. 80: 429-34 (1986).

Walker et al., "Chronic diabetic neuropathic foot ulcerations and total contact casting: healing effectiveness and outcome predictability", Arch. Phys. Med. Rehabil., vol. 66:574 (1985).

Wu et al., "The pivotal role of offloading in the management of neuropathic foot ulceration", Curr. Diab. Rep. vol. 5:423-9 (2005).

Wu et al., "Use of pressure offloading devices in diabetic foot ulcers", Diabetes Care, vol. 31(11):2118-2119, (2008).

* cited by examiner

INTELLIGENT DEVICE TO MONITOR AND REMIND PATIENTS WITH FOOTWEAR, WALKING AIDS, BRACES, OR ORTHOTICS

FEDERALLY SPONSORED RESEARCH

Not Applicable

SEQUENCE LISTING OR PROGRAM

Not Applicable

FIELD

This invention generally relates to body movement monitoring systems, and specifically to an ambulatory system which monitors whether the user is wearing and/or using his or her prescribed footwear, walking aid, braces (including knee and ankle braces) or other orthotics. The present invention 1) identifies the parameters related to the user's postures and movements (e.g., standing, walking, and running) and classifies the user's posture and foot loading condition using a body-worn sensor; 2) identifies whether the body-worn sensor is worn by the user; 3) detects whether the user is using any other tagged devices (such as prescribed footwear, walking aids, braces and orthotics) during foot loading conditions (e.g., walking or standing longer than 10 seconds) or specific postures; 4) in one embodiment, alerts the subject and/or the subject's caregivers if the user ambulates without a specified tagged device (e.g., without using the prescribed footwear or other walking aid); and 5) identifies the user's posture during time periods over which specified footwear are being worn or carried by the user.

BACKGROUND OF THE INVENTION

Objective, novel, and cost-effective approaches for assessing and improving patient adherence to treatment are in high demand. Of particular interest are methods for quantifying the patient's adherence to (and preference for) wearing therapeutic and prescribed footwear and offloading devices (collectively, "therapeutic footwear.") An exemplary use of such technology is for monitoring diabetic patients who have developed neuropathic foot ulcers and who must wear therapeutic footwear as the most important part of their healing regimen. In the field of diabetic foot ulcer prevention, knowledge of patient preference for specific types of footwear will aid developers improve the design of customized footwear, thus improving healing Patient adherence to wearing their therapeutic footwear can significantly enhance and improve healing. Although laboratory studies using total contact insoles and rocker-sole shoes have demonstrated modest reductions in pressure, these clinical footwear trials are inconclusive. Within 12 months, 26-42% of the studied patients had re-ulcerated. These results are likely due to lack of patient adherence to footwear. For example, despite taking a significant number portion of their daily steps at home (some studies have estimated this fraction to be over 50%), patients view their homes as "safe zone" where they typically do not wear prescribed footwear. As a result, high-risk patients wear their therapeutic footwear not as often as they should (some studies estimate that such patients wear the required footwear only 15-28% of the time).

What exacerbates the problem faced by such patients is that the methods used studies quantify patient adherence likely underestimate the patients' non-adherence to a significant degree. Adherence is typically measured through face-to-face interviews with a small number of patients. Previous investigations have shown that patients under-report "sensitive" conditions in face-to-face interviews versus telephone or paper surveys.

The present invention consists of a system for monitoring, assessing and improving patient adherence to any prescribed footwear.

Applied to diabetic care, the present invention can monitor patient adherence to instructions provided by caregivers—specifically for using a cast boot or other prescribed offloading devices and therapeutic footwear during walking, and/or foot loading condition. The invention can also remind and/or alert the patient if he or she forgets or neglects to use the prescribed footwear during standing and walking or other predefined movements. The invented system can promote the use of therapeutic footwear, socks or removable cast walkers (RCWs).

Foot ulceration is one of the most common precursors to lower extremity amputations among diabetics [3-5]. Ulcerations are pivotal events in limb loss for two important reasons: they provide a direct pathway for infection [6] and also cause progressive tissue necrosis and poor wound healing in the presence of ischemia. In diabetic adults, foot infections rarely develop in the absence of a wound. In this population, ulcers are the most common type of wound [6]. Foot ulcer, therefore, plays a central role in the causal pathway to lower extremity amputation [7].

Clearly, an effective treatment of foot ulcerations is critical to any plan for amputation prevention. Lowering of pressure, shear, and repetitive injury to the sole of the foot are fundamental to diabetic ulcer care.

Total Contact Casting (TCC) is considered the "ideal" gold standard to heal diabetic foot ulcers [8-12]. TCCs have been shown to reduce pressure at the site of ulceration by 84-92% [13]. Despite a significant body of clinical and laboratory work indicating their efficacy and safety, total contact casts are not widely used due to several practical barriers limiting their adoption by the general medical community. They are difficult to apply, expensive, and place significant demands on resources from busy clinics. Additionally, should the foot ulcer require re-examination, the TCC must be removed and then fully reapplied. Due to these disadvantages, an effective alternative to TCCs is needed.

SUMMARY OF THE INVENTION

The present invention enhances patient adherence by reminding the user and/or alerting caregivers if the patient moves without using the cast. This alarm function is useful to a significant number of patients who tend to remove treatment devices from their feet [14]. Although standard RCWs reduce peak pressures as effectively as TCCs [13], in both descriptive studies and randomized clinical trials TCCs achieve higher healing rates. A logical explanation for this is patient non-compliance to treatment.

In the fields of elderly care, physical medicine, and rehabilitation, the present invention can be used to measure adherence and remind patients to use various prescribed braces, orthotics, prostheses, and ambulatory aid devices during walking, movement or prescribed posture.

In clinical research and studies, the present invention provides valuable insight into the factors affecting patient compliance with prescribed footwear, walking aid devices, orthotics, and braces. Additionally, the present invention can help quantify the relationship between the usage of prescribed footwear, walking aids and orthotics with the user's state of health.

The present invention can also be used to gather data on the type of footwear being used and the duration of time spent in each body posture. This invention will provide insight into exactly what shoes are being worn for a specific activity by individuals. Such data enables the prescribing clinician to use more effective therapeutic or treatment strategies based on the patient's preferences for footwear and activity demands. It may also help manufacturers in their design and development of footwear.

In addition, the invented technology can provide key information about the user's activity pattern. For example, this invention can identify, for a given subject, the physical condition leading to least adherence with the caregiver's instructions. Such information, in turn, may lead to new regimens for improving patient adherence. By providing an alarm during undesired foot loading conditions, moreover, patient adherence may be improved significantly, thus minimizing complications during the treatment period. The alarm can be adjusted by the clinician. For example, the clinician can set the alarm when the subject's walking falls outside of a pre-defined range of parameters (e.g., 5 steps walking or 10 seconds standing) without wearing the prescribed footwear or offloading device.

DESCRIPTION OF THE PRESENT INVENTION

The present invention consists of a body movement monitoring system (see FIG. 1), including a sensor unit 103 comprising a multitude of accelerometers. The sensor unit may be either carried by the user 101 or attached to the user's body. The accelerometers may be mono- or multi-axial. If multi-axial, the accelerometers measure accelerations in perpendicular directions. The accelerometer data is used to detect the user's foot loading condition, posture (e.g., standing and walking) as well as his or her gait parameters.

The system and algorithms used in the present invention are robust and can be used independent of the placement of the sensor on the body. The system may provide information and alerts to cell phones and other aid devices such as auto-biofeedback or reminder systems.

The system includes one or more identifiable Radio Frequency Identification (RFID) tags 104 incorporated in or attached to said user's prescribed footwear 102, brace, orthotics or other walking aid device (FIG. 1). If the sensor detects the RFID tag to be out of range—as would be the case if the user 101 does not wear the footwear 102 incorporating the tag 104—and at the same time detects a foot loading condition (e.g., walking), it reminds the user 101 and/or alerts the clinical center (e.g., via radio-frequency (RF) communication).

The system includes an auditory and/or vibration alarm that can be used to alert the user 101 or the user's caregiver. Once the system detects a foot loading condition at the same time as an out-of-range RFID tag, it activates an alarm and/or a reminder system after the user 101 exceeds a threshold number of walking steps (e.g., 5 steps). The walking steps can be identified using the signals from the accelerometer(s), processed by algorithms developed to measure the walking period.

Some or all of the required analysis may be carried out on-board the sensor unit. In some cases, software-based algorithms, developed as part of the present invention, are integrated within the processor circuits performing the analyses. These algorithms can be used for real-time interventions.

The system also includes one or more data storage systems configured to store (log) signals recorded by said accelerometer(s), or the information derived by one of said processor circuits, or both, as well as the RFID data. One or more of said data storage systems may be housed within the sensor unit 103.

Additionally, the system allows identifying the period in which the sensor 103 is not worn at the chest level by assessing user's 101 respiration fluctuation. The sensor 101 may optionally include a selection switch for the user's 101 preferred mode of biofeedback (e.g., auditory/vibration; similar to sound/vibrate options available on cellular phones).

The algorithm used by the presentation invention consists of the several steps described below:

I. Gait Analysis and the Identification of Walking Periods

The first step performs a gait-analysis function, removing from the recorded data periods associated with postural transitions and lying. This algorithm is based on previous work described in reference [15].

Next, to attenuate the trunk rotational artifacts, the algorithm estimates the magnitude of tangential acceleration—i.e., the time-varying norm of the vertical and frontal accelerometers' signals. This allows for the suppression of the rotational components of trunk acceleration. The gravitational component may be removed, and the frontal acceleration signal may be reduced through wavelet transform with a filter—e.g., mother wavelet: db4, scales 2-5.

An algorithm using peak detection estimates the number of gait steps and cadence using the vertical accelerometer signal. A walking segment is defined where at least three successive peaks beyond a threshold are recognized at a pre-defined interval.

In addition, the system identifies right and left gait steps using the lateral accelerometer signal. During the recognized walking period, the lateral accelerometer output is integrated to obtain the lateral velocity. Comparison of the time location of the positive and negative peaks indicates the right-left sequence of the steps. The information from the step detection algorithm and the left and right step detection algorithm are used to identify left and right gait cycle times (right gait cycle time (n)=right step (n)+left step (n+1); left gait cycle time (n)=left step (n)+right step (n+1); here 'n' denotes the index of the identified step). This timing information is crucial to the detection of 'turning.' A turn is detected if the difference between the right gait cycle time and the left gait cycle time at time 'n' was exceeds a threshold.

II. Use of Respiration Fluctuation to Identify Whether the User has Worn the Sensor Unit.

The system includes algorithms implemented in the sensor unit 103 to measure and monitor the user's 101 adherence in wearing the body-worn motion sensor 103. These algorithms detect fluctuations in the acceleration data recorded by the sensor 103 due to user's 101 respiration. At rest, the fluctuation of the acceleration data due to respiration is identified by the algorithms (typically the standard deviation >0.005 g, FIG. 3b). When the sensor 103 is placed on a table, the acceleration fluctuation is close to zero and only white noise is recorded (typically the standard deviation <0.0005 g, FIG. 3c and FIG. 3d).

III. Using RFID Tags to Identify Whether the User has Worn the Prescribed Footwear The system includes an RFID tag reader (e.g., an RF unit) in the sensor unit 103 and one or more RFID tags 104 inside the prescribed footwear. The algorithm implemented by the processor on-board the sensor unit 103 first characterizes the type of foot loading condition 201 occurring at any instant of time. On this basis, the algorithm identifies periods of the walking 203 and/or standing 202 by categorizing the foot-loading condition. Identification of walking and its period is explained in Section I above.

If a foot-loading condition satisfying predefined criteria is identified (e.g., a duration more than 10 seconds for standing 204 or more than 10 steps during walking 205, the sensor unit scans the RFID tag(s) 104 (FIG. 2, 207). If the RFID tag(s) 104 is (are) out of range (FIG. 2, 208), the sensor unit sounds an alarm and/or stores the time instant at which this condition is first detected within the on-board memory of the sensor unit 103. The sensor unit 103 continues to rescan the presence of RFID tag(s) 104 in a predefined interval until the time when it either recognizes its (their) presence, or the user's 101 posture changes to a non-foot loading condition (e.g., sitting, lying, etc.)

Among the advantages of the present invention are the following:
a. RFID technology is inexpensive;
b. since the RFID tag 104 is light and small, it can be unobtrusively integrated into most types of shoes, insoles, or socks. This is unlike current instrumented shoes requiring room for bulky circuit boards;
c. the system identifies the adherence of the user 101 in wearing the sensor by measuring respiration fluctuation. Therefore, unlike other approaches, the system identifies whether the sensor unit 103 is being carried by the user 101;
d. the system will activate the RF component only in predefined activities, thereby minimizing the power requirements of the system, and enhancing battery life.

IV. Using the Optional Accelerometer in the Tagged Device(s) to Increase the Accuracy of the Device(s) in Evaluating Adherence to Prescribed Footwear The tagged device 102 may optionally include an accelerometer used to detect the user's 101 locomotion. In one embodiment of the invention, the user's 101 locomotion is identified using a peak-detection algorithm. If, during a predefined interval (approximately six seconds), at least three successive peaks exceeding a predefined threshold (approximately 0.1 g) are detected by the optional accelerometer, that interval is assumed to include locomotion by the user 101. Otherwise, the interval is assumed to not contain any locomotion (e.g., 'no locomotion'). In one embodiment, this information may be recorded in an embedded memory within the tagged device as a coded value of "1" for locomotion and "0" for "no locomotion." When the sensor unit identifies locomotion simultaneously with detecting the presence of the tagged device within a predefined distance of the sensor, the content of the memory on board the sensor unit 103 is checked to verify whether a locomotion event was also detected using the tagged device. If no-locomotion is recorded or detected by the tagged device, it is assumed that the tagged device has not been worn.

REFERENCES

Figure 1:
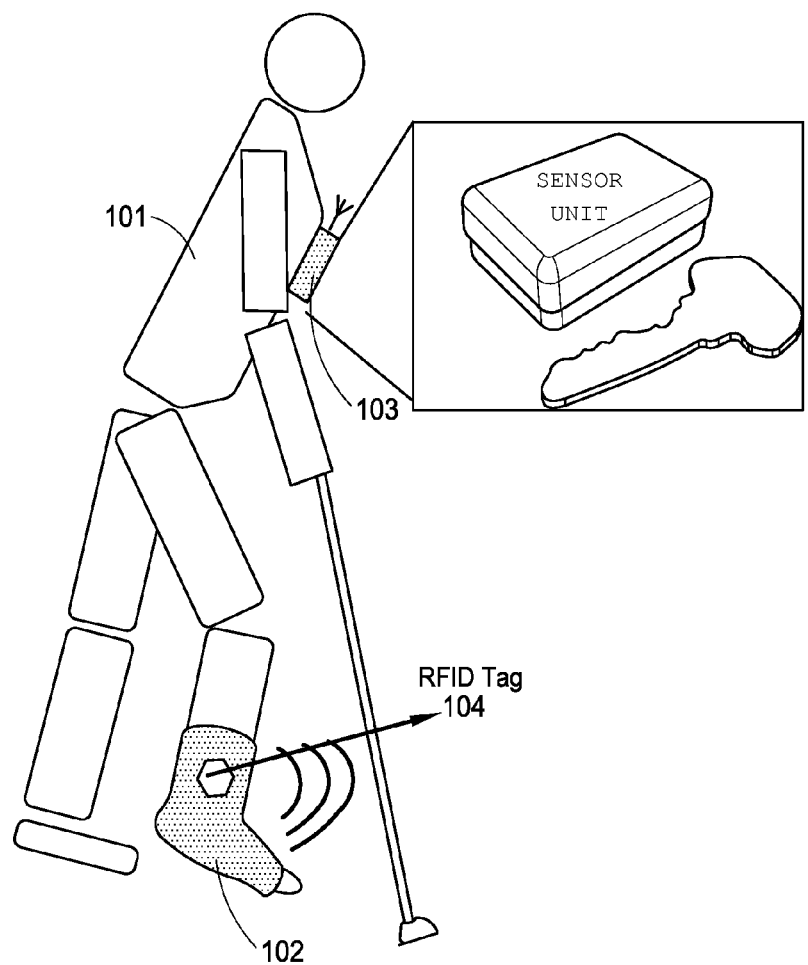
FIG. 1 is a schematic of the proposed system. The sensory unit is shown on the subject's chest in this figure. Generally, however, the sensory unit 103 may be either carried out by the user 101 or attached to his or her body.
Figure 2:
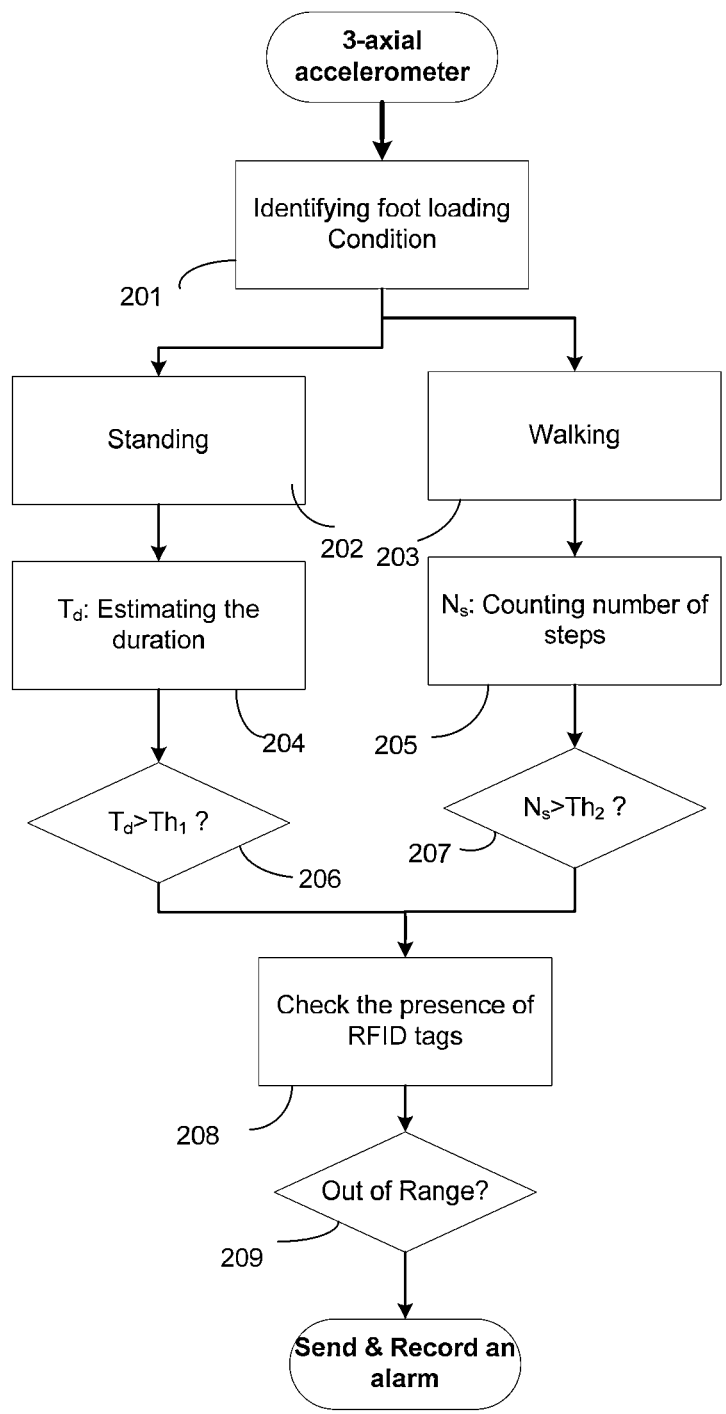
FIG. 2 is a flowchart of the algorithms used to identify the foot loading conditions, walking periods, and for computing the subject's spatiotemporal parameters of gait.
Figure 3:
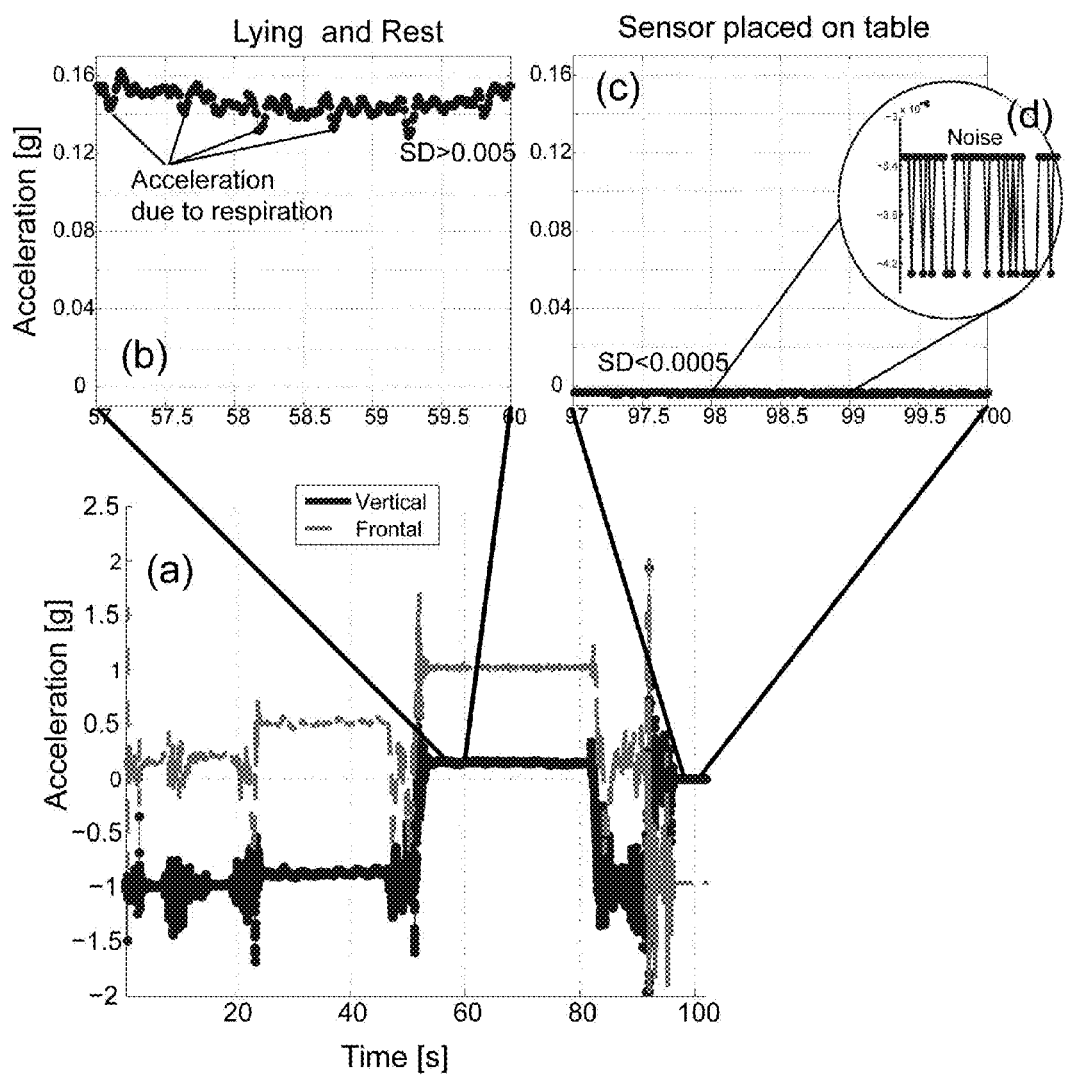
FIG. 3 illustrates an example of acceleration data (part a), including when the sensor was worn (part b); and when the sensor was placed on a table (parts c-d).

[1] D. G. Armstrong, P. L. Abu-Rumman, B. P. Nixon, and A. J. Boulton, "Continuous Activity Monitoring in Persons at High Risk for Diabetes-Related Lower-Extremity Amputation," *Journal of the American Podiatric Medical Association*, vol. 91, pp. 451-455, 2001.

[2] D. G. Armstrong, L. A. Lavery, S. Wu, and A. J. Boulton, "Evaluation of Removable and Irremovable Cast Walkers in the Healing of Diabetic Foot Wounds: a Randomized Controlled Trial," *Diabetes Care*, vol. 28, pp. 551-4, 2005.

[3] S. C. Wu, J. L. Jensen, A. K. Weber, D. E. Robinson, and D. G. Armstrong, "Use of Pressure Offloading Devices in Diabetic Foot Ulcers: Do We Practice What We Preach?" *Diabetes Care*, Aug. 11, 2008.

[4] S. C. Wu, R. T. Crews, and D. G. Armstrong, "The pivotal role of offloading in the management of neuropathic foot ulceration," *Curr Diab Rep*, vol. 5, pp. 423-9, December 2005.

[5] D. G. Armstrong, "Variability in Activity May Precede Diabetic Foot Ulceration," *Diabetes Care*, pp. 3028-3029, 2004.

[6] P. W. Brand, "The diabetic foot," in *Diabetes mellitus, theory and practice,* 3rd ed, Ellenberg M Rifkin H, Ed. New York: Medical Examination Publishing, 1983, pp. 803-828.

[7] R. E. Pecoraro, G. E. Reiber, and E. M. Burgess, "Pathways to diabetic limb amputation: basis for prevention," *Diabetes Care*, vol. 13, pp. 513-521, 1990.

[8] American Diabetes Association, "Consensus Development Conference on Diabetic Foot Wound Care," *Diabetes Care*, vol. 22, p. 1354, 1999.

[9] W. Coleman, P. W. Brand, and J. A. Birke, "The total contact cast, a therapy for plantar ulceration on insensitive feet," *J Am Podiatr Med Assoc*, vol. 74, pp. 548-552, 1984.

[10] P. A. Helm, S. C. Walker, and G. Pulliam, "Total contact casting in diabetic patients with neuropathic foot ulcerations," *Arch Phys Med Rehabil*, vol. 65, pp. 691-693, 1984.

[11] S. C. Walker, P. A. Helm, and G. Pulliam, "Chronic diabetic neuropathic foot ulcerations and total contact casting: healing effectiveness and outcome probability (abstract)." *Arch Phys Med Rehabil, vol.* 66, p. 574, 1985.

[12] D. R. Sinacore, M. J. Mueller, and J. E. Diamond, "Diabetic plantar ulcers treated by total contact casting," *Phys Ther*, vol. 67, pp. 1543-1547, 1987.

[13] L. A. Lavery, S. A. Vela, D. C. Lavery, and T. L. Quebedeaux, "Reducing dynamic foot pressures in high-risk diabetic subjects with foot ulcerations. A comparison of treatments," *Diabetes Care*, vol. 19, pp. 818-21, 1996.

[14] D. G. Armstrong, L. A. Lavery, H. R. Kimbriel, B. P. Nixon, and A. J. Boulton, "Activity Patterns of Patients With Diabetic Foot Ulceration: Patients with active ulceration may not adhere to a standard pressure off-loading regimen," *Diabetes Care*, vol. 26, pp. 2595-2597, September 2003.

[15] B. Najafi, A. Vaziri, and A. R. Boloori, "An Ambulatory System for Measuring and Monitoring Physical Activity and Risk of Falling and for Automatic Fall Detection; EFS ID: 2314530; Application number: 60979557," US-Patent, Ed., 2007.

[16] B. Najafi, J. Wrobel, and D. Armstrong, "A Novel Ambulatory Device For Continuous 24-H Monitoring Of Physical Activity In Daily Life," in *North American Congress on Biomechanics (NACOB)*, Michigan, 2008.

The invention claimed is:

1. A system for assessing and improving adherence of a user in wearing at least one of footwear, braces, or orthotics, or using walking-aid devices, the system comprising:
a sensor configured to be worn by said user, said sensor comprising one or more accelerometers; and one or more tagged devices identified by one or more radio-frequency tags and comprising one or more accelerometers;

wherein said system is configured to:
- detect whether said user is wearing said sensor at least partly in response to measurements of respiration fluctuation of said user using said one or more accelerometers of the sensor; and
- detect that said user is not wearing said one or more tagged devices at least partly by identifying instants or time periods when:
  - said one or more tagged devices are not detected by said sensor to be within a predefined distance of said sensor and measurements from said sensor indicate that said user undergoes a pre-specified foot-loading condition; or
  - measurements from said sensor indicate that said user is walking, said one or more tagged devices are detected by said sensor to be within said predefined distance of said sensor, and measurements from said one or more accelerometers of said one or more tagged devices do not indicate that said user is walking.

2. The system of claim 1, wherein the system is further configured to alert said user or a caregiver if said user moves without said one or more tagged devices.

3. The system of claim 1, wherein the system is further configured to record time periods when said user does not wear at least one of said one or more tagged devices or said sensor.

4. The system of claim 1, wherein the system is further configured to identify an activity pattern of said user.

5. The system of claim 1, wherein said sensor scans for said one or more tagged devices only during foot loading conditions.

6. A body movement monitoring system comprising:
a sensor configured to be on a part of a body of a person, the sensor comprising:
- at least a first accelerometer configured to generate at least one first signal indicative of acceleration corresponding to a movement of the body of the person; and one or more processor circuits programmed to:
- process the at least one first signal to detect a foot-loading condition of the person;
- determine whether a device usable by the person for treating a medical condition is within range of the sensor while the person is engaged in the foot-loading condition; and
- in response to determining that the device is not within range of the sensor during the detected foot loading condition, determine that the person is out of compliance with a treatment regimen associated with using the device.

7. The system of claim 6, wherein the sensor is further configured to generate at least one second signal indicative of a physiological parameter of the person, and wherein the one or more processor circuits are further programmed to:
- process the at least one second signal to determine whether the sensor is being worn by the person; and
- in response to detecting that the sensor is not being worn by the person, determine that the person is out of compliance with the treatment regimen.

8. The system of claim 7, wherein the physiological parameter comprises respiration fluctuation.

9. The system of claim 6, wherein the sensor further comprises a wireless identification reader, and wherein said one or more processor circuits determine whether the device is within range of the sensor in response to an output of the wireless identification reader which is indicative of whether a wireless identification tag of the device is within range of the sensor.

10. The system of claim 6, wherein the wireless identification reader scans for the wireless identification tag only during foot-loading conditions.

11. The system of claim 6, wherein upon determining that the person is out of compliance with the treatment regimen, the one or more processor circuits are configured to generate a command to provide an alert to the user.

12. The system of claim 6, wherein at least one second accelerometer is supported by the device and is configured to generate at least one third signal indicative of acceleration corresponding to the movement of the body of the person, and wherein the one or more processor circuits are further programmed to:
- process the at least one first signal to determine whether the at least one first signal indicates locomotion of the person during a first interval;
- process the at least one third signal to determine whether the at least one third signal indicates locomotion of the person during the first interval; and
- in response to determining that the at least one first signal indicates locomotion of the person during the first interval and that the at least one third signal does not indicate locomotion of the person during the first interval, determine that the person is out of compliance with the treatment regimen.

13. The system of claim 6, wherein the one or more processor circuits determine whether the device prescribed for use by the person is within range of the sensor at least partly by detecting whether a wireless identification tag supported by the device is in communication range of the sensor.

14. The system of claim 6, wherein the one or more processor circuits determine whether the device prescribed for use by the person is within range of the sensor at least partly by determining whether the device is within a predefined distance of the sensor.

15. The system of claim 6, wherein the device comprises footwear.

16. The system of claim 6, wherein the device comprises one or more of footwear, a walking aid, a knee brace, an ankle brace, a sock, or a removable cast walker.

17. The system of claim 6, wherein the device comprises an orthotic device.

18. A method of determining, by one or more processor circuits, compliance with a treatment regimen associated with a device, the method comprising:
- processing one or more signals from at least a first accelerometer of a sensor worn by a person to detect that the person is engaged in a foot-loading condition;
- determining whether a device usable by the person for treating a medical condition is within range of the sensor while the person is engaged in the foot-loading condition; and
- in response to determining that the device is not within range of the sensor while the person is engaged in the foot-loading condition, determining, by one or more processor circuits, that the person is out of compliance with a treatment regimen associated with using the device.

19. The method of claim 18, further comprising:
processing one or more signals generated by the sensor that are indicative of a physiological parameter of the person to determine whether the sensor is being worn by the person; and
in response to detecting that the sensor is not being worn by the person, determining that the person is out of compliance with the treatment regimen.

20. The method of claim 18, further comprising:
processing the one or more signals from the first accelerometer to determine whether the one or more signals from the first accelerometer indicate locomotion of the person during a first interval;
processing one or more signals from at least a second accelerometer supported by the device to determine whether the one or more signals from the second accelerometer indicate locomotion of the person during the first interval; and
in response to determining that the one or more signals from the first accelerometer indicate locomotion of the person during the first interval and that the one or more signals from the second accelerometer do not indicate locomotion of the person during the first interval, determining that the person is out of compliance with the treatment regimen.

21. The method of claim 18, wherein the device comprises one or more of footwear, a walking aid, a knee brace, an ankle brace, a sock, or a removable cast walker.

* * * * *